United States Patent
Mascal et al.

(10) Patent No.: US 10,647,670 B2
(45) Date of Patent: May 12, 2020

(54) PREPARATION OF COMPOUNDS FROM LEVULINIC ACID

(71) Applicant: THE REGENTS OF THE UNIVERSITY OF CALIFORNIA, Oakland, CA (US)

(72) Inventors: Mark Mascal, Oakland, CA (US); Saikat Dutta, Oakland, CA (US); Linglin Wu, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/547,041

(22) PCT Filed: Jan. 29, 2016

(86) PCT No.: PCT/US2016/015605
§ 371 (c)(1),
(2) Date: Jul. 27, 2017

(87) PCT Pub. No.: WO2016/123459
PCT Pub. Date: Aug. 4, 2016

(65) Prior Publication Data
US 2018/0029980 A1  Feb. 1, 2018

Related U.S. Application Data

(60) Provisional application No. 62/115,848, filed on Feb. 13, 2015, provisional application No. 62/109,787, filed on Jan. 30, 2015.

(51) Int. Cl.
| | | |
|---|---|---|
| *C07C 407/00* | (2006.01) | |
| *C07C 51/285* | (2006.01) | |
| *C07C 51/367* | (2006.01) | |
| *C07B 41/08* | (2006.01) | |
| *C07B 41/14* | (2006.01) | |
| *C07C 55/10* | (2006.01) | |
| *C07C 59/01* | (2006.01) | |
| *C07C 409/16* | (2006.01) | |

(52) U.S. Cl.
CPC ............ *C07C 407/00* (2013.01); *C07B 41/08* (2013.01); *C07B 41/14* (2013.01); *C07C 51/285* (2013.01); *C07C 51/367* (2013.01); *C07C 55/10* (2013.01); *C07C 59/01* (2013.01); *C07C 409/16* (2013.01)

(58) Field of Classification Search
None
See application file for complete search history.

(56) References Cited

U.S. PATENT DOCUMENTS

| | | | |
|---|---|---|---|
| 3,833,625 A | | 9/1974 | Bertrand et al. |
| 4,876,382 A | * | 10/1989 | Nishimura ............ C07C 45/008 560/109 |
| 5,892,107 A | * | 4/1999 | Farone .................... C07C 51/00 549/326 |
| 2014/0343305 A1 | | 11/2014 | Subramaniam et al. |

FOREIGN PATENT DOCUMENTS

| | | | | |
|---|---|---|---|---|
| WO | WO 2012044168 | * | 4/2012 | |
| WO | 2013033081 A2 | | 3/2013 | |
| WO | WO 2013159322 | * | 10/2013 | |
| WO | WO-2013159322 A1 | * | 10/2013 | ............ C07C 51/16 |
| WO | WO 2014150387 | * | 9/2014 | |
| WO | 2016123459 A1 | | 8/2016 | |

OTHER PUBLICATIONS

Caretto ("Upgrading of Levulinic Acid with Dimethylcarbonate as Solvent/Reagent" ACS Sustainable Chemistry and Engineering, 1, 2013, p. 989-994) (Year: 2013).*
Ponsford ("CXXVII. The oxidation of the fatty dibasic acids and of laevulic acid by hydrogen dioxide in presence of a cupric salt" Biochem J, 1934, 28, p. 892-897) (Year: 1934).*
Wu ("Efficient, Chemical-Catalytic Approach to the Production of 3-Hydroxypropanoic Acid by Oxidation of Biomass-Derived Levulinic Acid with Hydrogen Peroxide" ChemSusChem, 2015, 8, p. 1167-1169) (Year: 2015).*
Dutta ("Efficient, Metal-free production of succinic acid by oxidation of biomass-derived levulinic acid with hydrogen peroxide" Green Chemistry, 17, 2015, p. 2335-2338) (Year: 2015).*
Ponsford ("CXXVII. The Oxidation of the Fatty Dibasic Acids and of Leaveulic Acid by Hydrogen Dioxide in the Presence of a Cupric Salt", Biochem J. 1934, 28, p. 892) (Year: 1934).*

* cited by examiner

*Primary Examiner* — Amy C Bonaparte
(74) *Attorney, Agent, or Firm* — Mintz, Levin, Cohn, Ferris, Glovsky and Popeo, P.C.

(57) ABSTRACT

The present invention provides a method of making carboxylic acids from levulinic acid, such as succinic acid and 3-hydroxypropanoic acid, by reacting levulinic acid with an oxidant such as hydrogen peroxide under acidic or basic conditions.

3 Claims, No Drawings

PREPARATION OF COMPOUNDS FROM LEVULINIC ACID

CROSS-REFERENCES TO RELATED APPLICATIONS

This application claims priority to U.S. Provisional Application Nos. 62/115,848, filed Feb. 13, 2015, and 62/109,787, filed Jan. 30, 2015, each of which is incorporated in its entirety herein for all purposes.

BACKGROUND OF THE INVENTION

Succinic acid (SA) is an organic chemical of major commercial potential. Although the current market for SA is limited by its comparatively high price, it has been proposed as a feedstock for a variety of high-volume commodity chemicals, including 1,4-butanediol (BDO), gamma-butyrolactone (GBL), maleic anhydride (MA), and tetrahydrofuran (THF), among others. The recent description of biodegradable polypropylene succinate in the form of a stereocomplex with properties comparable to LDPE may also stimulate new commercial applications. SA is conventionally sourced via the $C_4$ stream of the light naphtha raffinate of petroleum, usually by hydrogenation of MA or maleic acid, or oxidation of BDO, although there are other approaches. Recently, however, a number of companies have begun producing SA via fermentative pathways with the goal of becoming competitive with petrochemical routes, such that the global demand for SA has been predicted to increase from the current <100 kT to >700 kT per annum by 2020, representing a ca. $1B market.

The biological route to succinic acid is centered around native overproduces bacteria and genetically engineered *E. coli*. Carbon sources are typically sugars, which may be derived from lignocellulose hydrolysates. Although generally good yields and productivity have been reported, challenges associated with downstream processing, including selectivity issues, the use of bases as neutralizing agents, and product isolation complicate the overall economics of the process.

In principle, chemical-catalytic pathways offer much faster and more scalable routes to SA from carbohydrates. Although no practical access to SA directly from raw biomass has yet been developed, approaches via furfural and levulinic acid, both one step removed from biomass, have been described. Thus, Choudhary et al. recently reported the oxidation of furfural, a derivative of hemicellulose, with $H_2O_7$ at 80° C. over 24 hours to give SA in up to 74% yield. However, the SA was contaminated with a maleic acid by-product and the reaction is dependent on an ultimately degradable catalyst (Amberlyst-15) (*Chem. Lett* 2012, 41, 409). Beyond this, the cost of the feedstock and long reaction period give little advantage over fermentative routes. Related methods involving furfural and other furans using a range of oxidants and catalysts generally give SA in lower yields and selectivities, and are described in reviews.

Levulinic acid (LA) is a renewable feedstock of exceptional promise. Unlike furfural, LA can be derived both from hemicellulose and the major, cellulosic fraction of carbohydrates. It can be produced in high yield via the acidic processing of biomass, and although this is practiced commercially only on a limited scale at present, economic projections have indicated that the production costs of LA could fall as low as $0.04-$0.10/lb. LA can also be accessed in high yield by the hydrolysis of the biomass derived platform molecule 5-(chloromethyl)furfural (CMF). As such, the potential of LA to unlock key renewable markets is vast.

The conversion of LA to SA was first described in a paper by Tollens as early as 1879. Nitric acid was employed as the oxidant, resulting in a mixture of organic acids, including SA, albeit in low yield (*Chem. Ber.* 1879, 12, 334). The first report of the action of hydrogen peroxide on LA was published in 1934, which described a reaction at 60° C. in the presence of a cupric salt catalyst, again giving a mixture of carboxylic acids but only trace SA (*Biochem. J.* 1934, 28, 892). U.S. Pat. No. 2,676,186 reported the gas phase oxidation of LA with $O_2$ and a vanadium catalyst at 375° C., wherein a maximum yield of 83% was claimed. This approach might have been of preparative interest were not the conditions so severe.

The current emphasis on green chemical production has led to a renewed interest in the conversion of LA to SA, and a flurry of recent publications describing this reaction has appeared. Thus, WO 2012/044168 describes the heating of LA with nitric acid-$NaNO_2$ at 40° C. for 4 h to give mixtures of SA and oxalic acid, the former in up to 52% yield. Liu et al. reported the application of a Mn(ITT) catalyst in the oxidation of methyl levulinate at 90° C. under 5 bar of $O_2$ to give a mixture of dimethyl succinate, malonate, and oxalate esters, along with related acetal derivatives (*ChemSusChem* 2013, 6, 2255). The maximum yield of succinate was 52% in a 20 hour reaction. Podolean et al. employed Ru(III) functionalized silica-coated magnetic nanoparticles under 10 bar $O_2$ at 150° C. for 6 hours in the conversion of LA to SA, where catalyst recycling experiments demonstrated good reusability (×3) at conversions of 54-58% and a 4% loading of ruthenium (*Green Chem.* 2013, 15, 3077). Finally, an interesting reaction was reported by Caretto and Perosa that involved simple heating of LA in a dimethylcarbonate/base mixture at 200° C. for 4 h to give dimethyl succinate among a range of other products in up to 20% yield (*Sustainable Chem. Eng.* 2013, 1, 989).

What is needed is a process that overcomes the modest yields, poor selectivity, severe conditions, and/or potentially foulable catalysts in the prior processes. Surprisingly, the present invention meets this and other needs.

3-Hydroxypropanoic acid (HPA) is considered a renewable target molecule of enormous latent potential, due to the fact that it provides a direct entry into the vast market for acrylic acid and its derivatives, while at the same time unlocking the bio-compatible/degradable HPA homopolymer market, which also shows much promise. The production of HPA from biomass sources is described in the literature almost exclusively by means of fermentation of glucose or glycerol. Although advances have been made, particularly in the development of recombinant yeast as producers, a number of technical hurdles remain, particularly associated with performance and downstream processing. HPA can also be produced via petrochemical approaches which have generally involved the hydration of acrylic acid or oxidation of allylic alcohol or propanediol, but current initiatives place a greater premium on the production of chemical drop-ins from renewable resources, rather than making biochemicals from petroleum.

In principle, chemical-catalytic pathways offer much faster and more scalable routes to HPA from carbohydrates than fermentative approaches, and a straightforward opportunity for the production of HPA from biomass appeared to present itself in the selective oxidation of levulinic acid (LA). We reasoned that if the selectivity of the oxidation of LA to SA with hydrogen peroxide could be reversed to favor the alternative migration product, a complementary route to HPA would also be forthcoming. Surprisingly, the present invention provides the analogous conversion of LA into HPA using $H_2O_2$ under modified reaction conditions.

BRIEF SUMMARY OF THE INVENTION

In one embodiment, the present invention provides a method of preparing a carboxylic acid, including forming a reaction mixture comprising levulinic acid, an oxidant, and an acid or a base, under conditions suitable to prepare the carboxylic acid.

In another embodiment, the present invention provides a method of preparing succinic acid, including forming a reaction mixture comprising levulinic acid, an oxidant and an acid, thereby preparing the succinic acid.

In another embodiment, the present invention provides a method of preparing 3-hydroxypropanoic acid, including forming a reaction mixture comprising levulinic acid, an oxidant, and a base, under conditions suitable to form the 3-hydroxypropanoic acid.

In another embodiment, the present invention provides a method of preparing 3-hydroxypropanoic acid, including forming a reaction mixture comprising levulinic acid, an oxidant, and a base, wherein the reaction mixture is at a temperature between about 75° C. and about 200° C., thereby forming 3-hydroxypropanoic acid.

In another embodiment, the present invention provides a method of preparing 3-hydroxypropanoic acid, including forming a reaction mixture comprising levulinic acid, an oxidant, and a base, wherein the reaction mixture is at a temperature between about 0° C. and about 50° C., thereby forming 3-(hydroperoxy)propanoic acid, and forming a second reaction mixture comprising the 3-(hydroperoxy)propanoic acid and a hydrogenation agent, under conditions suitable to form the 3-hydroxypropanoic acid.

DETAILED DESCRIPTION OF THE INVENTION

I. General

The present invention describes methods of preparing carboxylic acids from biomass. For example, levulinic acid mixed with an oxidant such as hydrogen peroxide, and an acid or a base, is capable of preparing commercially valuable compounds such as succinic acid and 3-hydroxypropanoic acid. When an acid is combined with the levulinic acid and hydrogen peroxide, the carboxylic acid can be succinic acid. When a base is combined with the levulinic acid and hydrogen peroxide, the carboxylic acid can be 3-hydroxypropanoic acid. The 3-hydroxypropanoic acid can be prepared directly from the levulinic acid when the reaction temperature is about 100° C. The 3-hydroxypropanoic acid can also be prepared at room temperature in a two-step process by first preparing 3-(hydroperoxy)propanoic acid, followed by reaction of the 3-(hydroperoxy)propanoic acid with a hydrogenation agent.

II. Definitions

"Forming a reaction mixture" refers to the process of bringing into contact at least two distinct species such that they mix together and can react, either modifying one of the initial reactants or forming a third distinct species, i.e., a product. It should be appreciated, however, that the resulting reaction product can be produced directly from a reaction between the added reagents or from an intermediate from one or more of the added reagents which can be produced in the reaction mixture.

"Acid" refers to a compound that is capable of donating a proton ($H^+$) an under the Bronsted-Lowry definition, or is an electron pair acceptor under the Lewis definition. Acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, camphorsulfonic acid, among others. Strong acid" refers to acids having a $pK_a$ generally less than about 1.0. Representative strong acids include, but are not limited to, trifluoroacetic acid, triflic acid, methanesulfonic acid, p-toluenesulfonic acid, hydrochloric acid, sulfuric acid, and nitric acid.

"Oxidant", "oxidizing agent" or "oxidizer" all refer to any non-metal agent capable of oxidizing an organic compound, such as an alcohol to a carboxylic acid. Representative oxidants include, but are not limited to, inorganic peroxides such as hydrogen peroxide, organic peroxides such as perbenzoic acid, nitric acid, sulfuric acid, and others. The oxidant of the present invention does not include an oxidizing metal catalyst, such as an oxidizing agent containing a metal such as any transition metal. Representative transition metals include, but are not limited to, chromium, manganese, ruthenium, vanadium or osmium. Representative oxidizing metal catalysts include, but are not limited to, $MnO_4^-$ (permanganate), $CrO_4^{2-}$ (chromate), and $OsO_4$ (osmium tetroxide).

"Base" refers to a compound capable of accepting a proton ($H^+$) under the Bronsted-Lowry definition, or is an electron-pair donor under the Lewis definition. Bases useful in the present invention that are Bronsted-Lowry bases include hydroxides such as lithium hydroxide, sodium hydroxide, potassium hydroxide, rubidium hydroxide, cesium hydroxide, magnesium hydroxide, strontium hydroxide, barium hydroxide, and others. "Strong base" refers to bases having conjugate acids with a $pK_a$ generally greater than about 13.

"Room temperature" refers to a temperature of 20° C. to 25.5° C.

"Hydrogenation agent" refers to agents capable of the addition or insertion of molecular hydrogen ($H_2$) or the donation of a hydride ($H^-$). Representative hydrogenation agents include, but are not limited to, hydrogen gas plus a hydrogenation catalyst such as palladium on carbon (Pd/C), lithium aluminum hydride, sodium hydride, sodium borohydride, sodium cyanoborohydride, etc.

III. Method of Preparing a Carboxylic Acid

The present invention provides a method of preparing a carboxylic acid by combining levulinic acid, an oxidant, and an acid or a base. In some embodiments, the present invention provides a method of preparing a carboxylic acid, including forming a reaction mixture comprising levulinic acid and an oxidant, under conditions suitable to prepare the carboxylic acid.

The carboxylic acid can be any suitable carboxylic acid. For example, the carboxylic acid can be a $C_{3-4}$ carboxylic acid. In some embodiments, the carboxylic acid has the formula:

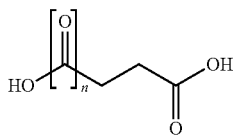

wherein n is 0 or 1. In some embodiments n is 0. In some embodiments, n is 1. In some embodiments, the carboxylic acid is succinic acid or 3-hydroxypropanoic acid.

The oxidant can be any suitable oxidant, other than an oxidizing metal catalyst. In some embodiments, the oxidant can be hydrogen peroxide.

The reaction mixture is substantially free of an oxidizing metal catalyst. Oxidizing metal catalysts can be manganese, chromium, osmium, ruthenium, and other metals.

In some embodiments, the present invention provides a method of preparing a carboxylic acid, including forming a reaction mixture comprising levulinic acid, an oxidant, and an acid or a base, wherein the reaction mixture is substantially free of an oxidizing metal catalyst, under conditions suitable to prepare the carboxylic acid. In some embodiments, the present invention provides a method of preparing a carboxylic acid, including forming a reaction mixture comprising levulinic acid, hydrogen peroxide, and an acid or a base, wherein the reaction mixture is substantially free of an oxidizing metal catalyst, under conditions suitable to prepare the carboxylic acid.

A. Preparation of Succinic Acid

In some embodiments, the carboxylic acid can be succinic acid. Succinic acid, also known as butanedioic acid, has the following structure:

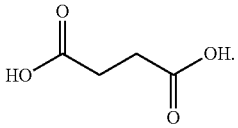

Hydrogen peroxide is identified as a reagent for the oxidation of LA due to its well-known Baeyer-Villiger type mechanism of action (Scheme 1).

Scheme 1. Oxidation of LA to SA with $H_2O_2$.

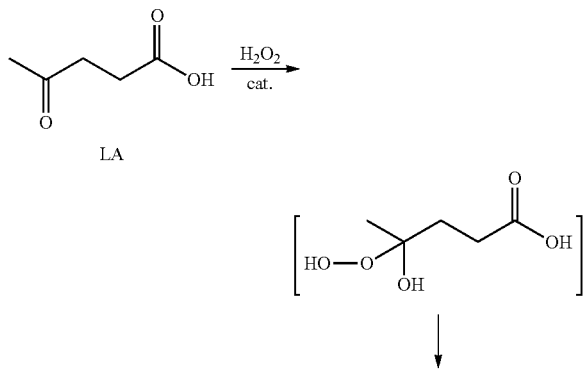

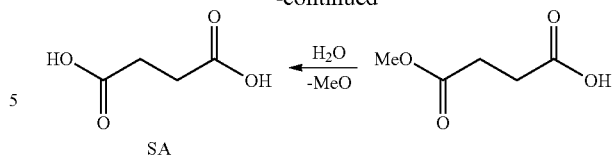

Initial experiments with $H_2O_2$ in aqueous sulfuric acid showed promise, giving a mixture of SA (48%), acetic acid (50%), formic acid (24%), and methanol (17%) (estimated yields by $^1$H NMR integration). Considering the reaction in Scheme 1, methanol is an expected byproduct, and the strong oxidizing conditions also lead to the conversion of LA to acetic acid. This chemistry is precedented—in fact, WO 2013/159322 uses LA as a feedstock for producing acetic acid with a range of oxidants, including $H_2O_2$. Formic acid is also seen in some cases as a byproduct. The observation of acetic acid can be explained as shown in Scheme 2 by invoking the alternative migration product in the Baeyer-Villiger oxidation, i.e. 3-hydroxypropanoic acid (HPA), as an intermediate. The conversion of LA to HPA co-produces a molecule of acetic acid on hydrolysis of the initially formed ester. HPA can then undergo a retro aldol cleavage (RA) to give acetic acid and formaldehyde, the latter ultimately being oxidized to formic acid.

Scheme 2. Oxidation of LA to acetic and formic acids with $H_2O_2$.

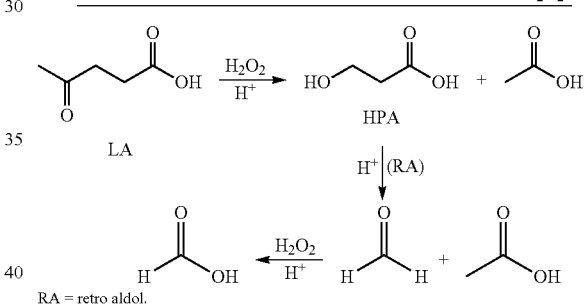

RA = retro aldol.

While the acetic acid, formic acid, and methanol are volatile and can be removed from the reaction mixture, separation of the SA product from aqueous sulfuric acid is difficult, and the recycle of sulfuric acid is costly. A solution to these issues presented itself in the form of trifluoroacetic acid (TFA) which, with $pK_a$ of ca. 0, was found to be sufficiently acidic to catalyze the reaction (*Chem. Phys. Lett.* 2008, 451, 163). Thus, when a mixture of LA and 30% aqueous $H_2O_2$ in TFA was heated at 90° C., the starting material was consumed within 2 hours and the result was a 62% yield of SA, alongside 43% acetic acid, 45% formic acid, and 9% HPA (estimated yields by $^1$H NMR integration). The initially formed monomethyl ester of SA transesterifies with TFA to give methyl trifluoroacetate (45%), which is captured in a cold trap. The volatile part of the reaction mixture thus consists of TFA methyl ester (bp 43° C.), TFA (bp 72° C.), the TFA-water azeotrope (79 wt % TFA, bp 105° C.) and finally acetic acid (bp 118° C.). The residual, white solid mass can be triturated with ether, in which SA is largely insoluble, to give pure SA (60% isolated yield). A scaled up reaction starting with 10.0 g of LA provided 6.0 g of SA (59%). The triturate includes HPA, a small amount of SA, and a mixture of unidentified, minor products.

The management of the TFA would be an important aspect of this process from an applied perspective. Taking the larger scale reaction (processing 10.0 g LA feedstock) as an example, the total 50 mL of 30% $H_2O_2$ used is capable of delivering a maximum of 48 g $H_2O$. The 200 mL of TFA used corresponds to 298 g, of which 180 g will combine with the 48 g of $H_2O$ to form 228 g of the azeotrope, with a remainder of 118 g TFA. While 30% aq $H_2O_2$ was used in this work, 50% $H_2O_2$ is generally available, with industrial concentrations up to 70%. For the 50% and 70% grades, the delivery of less water with the same quantity of $H_2O_2$ would result in the formation of 121 g and 76 g of the azeotrope, respectively, from which 25.5 and 16 g of water would need to be removed. Recycling of TFA is accomplished by dehydration of the azeotrope by membrane pervaporation. The above reaction was performed using 50% $H_2O_2$ with no significant variation in outcome.

In some embodiments, the method includes forming the reaction mixture comprising levulinic acid, the oxidant and an acid, thereby preparing the succinic acid. The reaction in the methods of the invention can be conducted at any suitable temperature. In general, reactions are conducted at temperatures ranging between about 20° C. and about 200° C. A reaction can be conducted, for example, at from about 20° C. to about 100° C., or from about 30° C. to about 100° C., or from about 40° C. to about 100° C., or from about 50° C. to about 100° C. A reaction can be conducted at about 20, 25, 30, 35, 40, 45, 50, 55, 60, 65, 70, 75, 80, 85, 90, 95, 100, 105, 110, 115, 120, 125, 130, 135, 140, 145, 150, or about 155° C. In some embodiments, the temperature can be about 90° C.

In some embodiments, the method includes forming the reaction mixture comprising levulinic acid, the oxidant and an acid, and heating the reaction mixture at a temperature of from about 30° C. to about 100° C., thereby preparing the succinic acid.

Any suitable non-metal oxidant can be used in the method of making succinic acid. In some embodiments, the oxidant can be hydrogen peroxide.

Any suitable acid can be used in the method of the present invention. Representative acids include organic acids such as carboxylic acids and halogenated carboxylic acids, mineral acids such as sulfuric acid, sulfonic acids such as methanesulfonic acid, and others. The acids can be strong acids, i.e., acids having a pKa less than about 1. In some embodiments, the acid can be a strong acid. In some embodiments, the acid can be hydrofluoric acid, hydrochloric acid, hydrobromic acid, hypochloric acid, perchloric acid, sulfuric acid, nitric acid, phosphoric acid, hexafluorophosphoric acid, methanesulfonic acid, benzenesulfonic acid, p-toluenesulfonic acid, trifluoromethanesulfonic acid, fluoroacetic acid, or trifluoroacetic acid. In some embodiments, the acid can be sulfuric acid or trifluoroacetic acid. In some embodiments, the acid can be sulfuric acid. In some embodiments, the acid can be trifluoroacetic acid.

In some embodiments, the method includes forming the reaction mixture comprising levulinic acid, trifluoroacetic acid, and hydrogen peroxide, and heating the reaction mixture at a temperature of from about 50° C. to about 100° C., thereby preparing succinic acid.

Any suitable solvent can be used in the methods of the invention. Suitable solvents include, but are not limited to, diethyl ether, diisopropyl ether, ethyl acetate, pentane, hexane, heptane, cyclohexane, benzene, toluene, chloroform, dichloromethane, carbon tetrachloride, 1,2-dichloroethane, 1,1-dichloroethane, N,N-dimethylformamide, N,N-dimethylacetamide, dimethylsulfoxide, N-methyl 2-pyrrolidone, acetic acid, trifluoroacetic acid, trichloroacetic acid, methyl ethyl ketone, methyl isobutylketone, acetonitrile, propionitrile, 1,4-dioxane, sulfolane, 1,2-dimethyoxyethane, and combinations thereof.

Any suitable reaction time can be used in the methods of the invention. In general, reactions are allowed to run for a time sufficient for consumption of the starting material and conversion to the desired product, or until conversion of the starting material comes to a stop. Reactions are typically allowed to run for any amount of time ranging from a few minutes to several hours. Reactions can be run, for example, for anywhere between 5 minutes and 48 hours. Reactions can be run for about 5 minutes, or about 10, 15, 20, 30, 45, 60, or more minutes. Reactions can be run for about 1, 2, 3, 4, 5, or more hours.

B. Preparation of 3-Hydroxypropanoic Acid

As discussed above, hydrogen peroxide is identified as a reagent of great potential for the oxidation of LA due to its well-known Baeyer-Villiger-type mechanism of action, that could in fact lead either to SA or HPA, depending on which group undergoes migration. Running the reaction under acidic conditions favors methyl group migration to give SA in good yield. Surprisingly, the selectivity of the migration could be controlled by switching the pH of the medium from acidic to basic. Thus, LA was dissolved in 30% aq. $H_2O_2$ and potassium hydroxide was added. The reaction was heated to 115° C. and further portions of base and $H_2O_2$ were added over the course of about 10 minutes. Unlike the same reaction in acid, rapid evolution of oxygen was observed at each addition. The mixture was allowed to stir undisturbed for a period of time before a final portion of $H_2O_2$ and KOH was added. The entire process was complete within about 90 minutes. Quantitative analysis by NMR using an internal standard showed that HPA was being produced in 47% yield. The mass balance consisted of acetic acid (89%), formic acid (29%), and methanol (9%). A volatiles trap further detected traces of acetone (ca. 1%). Running the same reaction at a lower temperature (60° C.) reduces the yield of HPA (22%) but increases the yield of acetone (10%).

Scheme 3. Baeyer-Villiger oxidation of LA with $H_2O_2$.

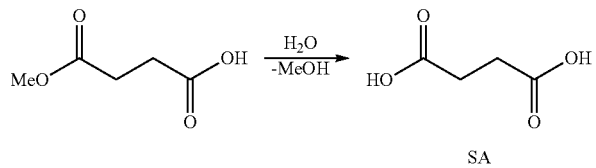

SA

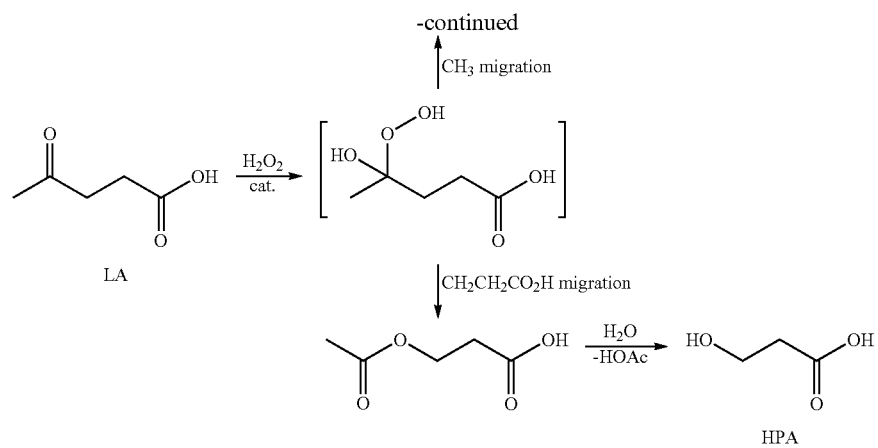

The range of observed products indicated that processes other than those shown in Scheme 3 are operative in this chemistry. Specifically, the fact that more acetic acid is produced than HPA demonstrates that more than one route to this product is available. The most likely scenario is oxidation of the enolate of LA to give 3-hydroxylevulinic acid (3HLA) (Scheme 4). Retro aldol cleavage of 3HLA yields acetate and methylglyoxal (MG). Baeyer-Villiger oxidation of MG is favored at the keto group, since the aldehyde exists mainly in the form of a hydrate. Methyl migration leads to the glyoxylic acid ester, which hydrolyzes to glyoxylate (GA), which itself breaks down on further oxidation to formate and $CO_2$. An alternative pathway involving dehydration of 3HLA and rehydration to 2-hydroxylevulinic acid (2HLA) can also be proposed. Retro aldol of 2HLA yields acetone and again GA. To test these mechanistic postulates, an independent sample of MG was submitted to the reaction conditions and in fact, only formate and methanol were observed in the NMR spectrum. A sample of GA produced only formate under the same conditions. The observation of methanol may also derive from Baeyer-Villiger oxidation of acetone and subsequent hydrolysis of the methyl acetate product.

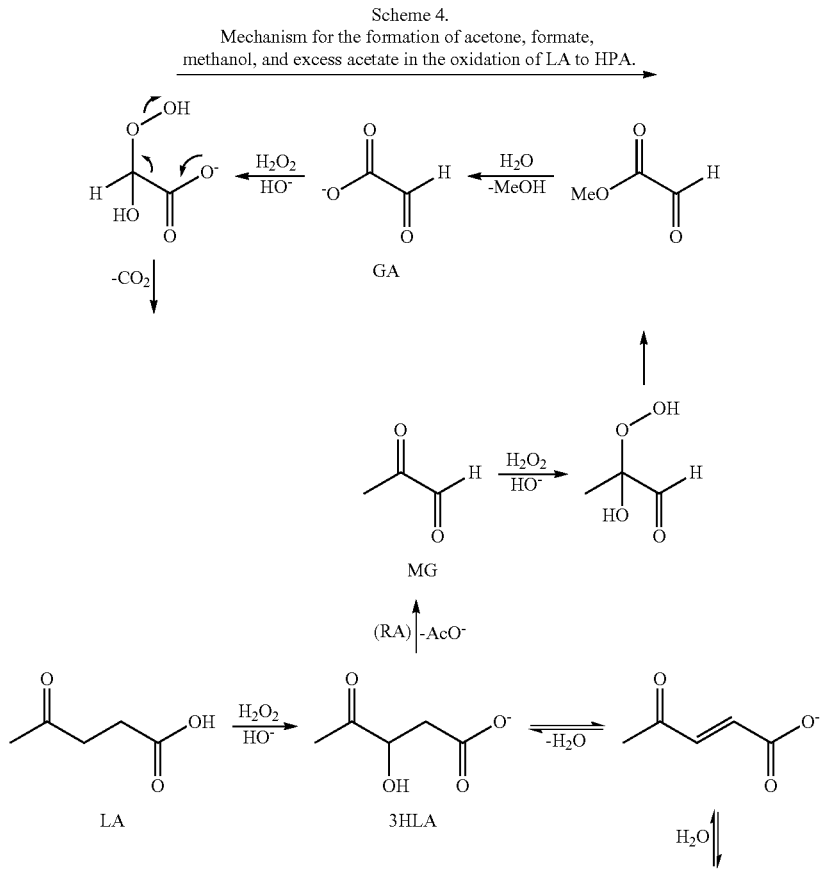

Scheme 4.
Mechanism for the formation of acetone, formate, methanol, and excess acetate in the oxidation of LA to HPA.

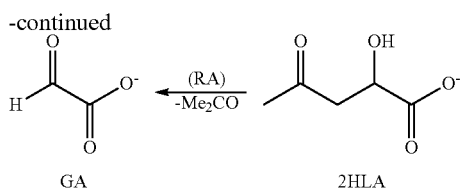

GA ← (RA), -Me₂CO — 2HLA

RA = retro aldol.

A by-product was observed in the reaction conducted at 60° C. which was not detected in the higher temperature process. It appeared similar to HPA but showed a greater downfield shift of the methylene group adjacent to oxygen in the $^1$H NMR. This was the corresponding hydroperoxide, i.e. 3-(hydroperoxy)propanoic acid (HPPA), confirmed by iodometric titration and by derivatization with MeI and Ag$_2$O to give methyl 3-(methylperoxy) propanoate. The yield of HPPA at 60° C. was low, but further reducing the Two pathways for the generation of HPPA are proposed, one or both of which may be operative. First, it is possible that, instead of hydrolysis of the acetate, elimination to an acrylate intermediate may occur as shown in Scheme 5. The higher nucleophilicity of hydroperoxide anion may explain the selectivity for HPPA over HPA in this lower temperature reaction. Alternatively, attack on the acetate carbonyl by hydroperoxide anion would give a tetrahedral intermediate which could rearrange as shown to give HPPA and acetate.

Scheme 5. Mechanisms for the formation of HPPA by oxidation of LA with H2O2.

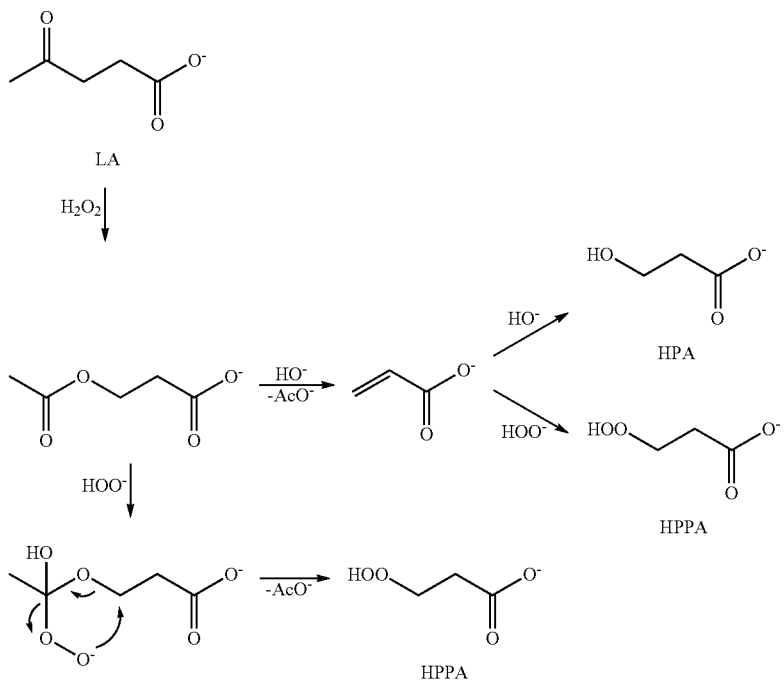

reaction temperature appeared to favor this product. Ultimately, it was found that carrying out the reaction between 0° C. and room temperature over the course of about 6 h resulted in the production of HPPA in 82% yield by $^1$H NMR integration, which was confirmed by isolation of the product in 80% yield. The expected, equivalent yield of acetic acid (80%) was also observed, alongside HPA (5%) and formic acid (4%). To avoid distillation of water in the isolation of HPPA, the product was isolated by continuous extraction with ether. Conversion of HPPA to HPA by O—O bond hydrogenolysis over Pd/C was facile and quantitative, and hence this approach to HPA is considered to be the method of choice.

The present invention provides a new concept for the derivation of 3-hydroxypropanoic acid from biomass. The process is fully chemical-catalytic, comparatively fast (vs. fermentation), operates under mild conditions, and gives HPA in high yield (>80% overall from LA). The mass balance of the reaction consists mainly of acetic acid, which is itself a useful commodity chemical. Since LA can be derived from raw cellulosic biomass in high yield, this practical, two-step method appears highly attractive for the industrial production of renewable acrylate derivatives, other C$_3$ chemicals (e.g. 1,3-propanediol, malonic acid), and the HPA homopolymer, while completely avoiding fermentation pathways.

In some embodiments, the present invention provides a method of preparing 3-hydroxypropanoic acid. The compound 3-hydroxypropanoic acid has the following formula:

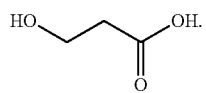

In some embodiments, the present invention provides a method of preparing 3-hydroxypropanoic acid, including forming a reaction mixture comprising levulinic acid, an oxidant, and a base, under conditions suitable to form the 3-hydroxypropanoic acid. In some embodiments, the method includes forming the reaction mixture comprising levulinic acid, the oxidant, and a base, under conditions suitable to form the 3-hydroxypropanoic acid.

Bases useful in the method of making 3-hydroxypropanoic acid include strong bases with conjugate acids having a pKa greater than about 13. Representative bases include, but are not limited to, lithium hydroxide, sodium hydroxide, potassium hydroxide, rubidium hydroxide, cesium hydroxide, magnesium hydroxide, strontium hydroxide, barium hydroxide, and others. In some embodiments, the strong base can be sodium hydroxide or potassium hydroxide. In some embodiments, the strong base can be potassium hydroxide.

The method of forming 3-hydroxypropanoic acid can be conducted at any suitable temperature. In general, reactions are conducted at temperatures ranging between about 0° C. and about 200° C. A reaction can be conducted, for example, at from about 25° C. to about 200° C., or from about 50° C. to about 200° C., or from about 75° C. to about 200° C., or from about 100° C. to about 150° C. A reaction can be conducted at about 20, 25, 30, 35, 40, 45, 50, 55, 60, 65, 70, 75, 80, 85, 90, 95, 100, 105, 110, 115, 120, 125, 130, 135, 140, 145, 150, or about 155° C. In some embodiments, the temperature can be about 115° C.

In some embodiments, the reaction mixture can be at a temperature between about 75° C. and about 200° C. In some embodiments, the reaction mixture can be at a temperature between about 100° C. and about 150° C. In some embodiments, the method of making 3-hydroxypropanoic acid includes forming the reaction mixture comprising levulinic acid, hydrogen peroxide, and potassium hydroxide, wherein the reaction mixture is at a temperature between about 100° C. and about 150° C., thereby forming the 3-hydroxypropanoic acid.

Alternatively, the temperature of the reaction mixture for preparing the 3-hydroxypropanoic acid can be between about 0° C. and about 50° C. A reaction can be conducted, for example, at from about 0° C. to about 50° C., or from about 0° C. to about 30° C., or from about 20° C. to about 30° C., or from about 0° C. to about 25° C. A reaction can be conducted at about 0, 5, 10, 25, 30, 35, 40, 45, or about 50° C. In some embodiments, the temperature can be about room temperature. In some embodiments, the temperature can be less than about room temperature.

In some embodiments, the reaction mixture can be at a temperature between about 0° C. and about 50° C. such that the product of the forming step is 3-(hydroperoxy)propanoic acid, and the method also includes forming a second reaction mixture comprising the 3-(hydroperoxy)propanoic acid and a hydrogenation agent, under conditions suitable to form the 3-hydroxypropanoic acid. The compound 3-(hydroperoxy)propanoic acid has the following structure:

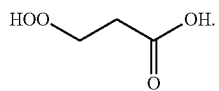

Any suitable hydrogenation agent can be used in the method of reducing 3-(hydroperoxy)propanoic acid to form 3-hydroxypropanoic acid. Hydrogenation agents are preferably non-nucleophilic. Representative hydrogenation agents include, but are not limited to, palladium on carbon. In some embodiments, the hydrogenation agent can be palladium on carbon. In some embodiments, the second reaction mixture also includes hydrogen gas. In some embodiments, the hydrogenation agent can be palladium on carbon and hydrogen gas. In some embodiments, the method of forming 3-hydroxypropanoic acid includes forming the reaction mixture comprising levulinic acid, hydrogen peroxide, and potassium hydroxide, wherein the reaction mixture is at about room temperature, thereby preparing 3-(hydroperoxy)propanoic acid; and forming the second reaction comprising the 3-(hydroperoxy)propanoic acid, hydrogen gas and palladium on carbon, under conditions suitable to form the 3-hydroxypropanoic acid.

Other steps are useful in the method of making 3-hydroxypropanoic acid. For example, the reaction mixture containing 3-(hydroperoxy)propanoic acid can be neutralized using acid, and then the 3-(hydroperoxy)propanoic acid can be isolated via extraction. In some embodiments, the method of preparing 3-hydroxypropanoic acid includes, prior to the second forming step, contacting the reaction mixture with an acid such that the pH of the reaction mixture is less than 7.0, and isolating the 3-(hydroperoxy)propanoic acid via extraction.

Any suitable acid can be used in the contacting step to neutralize the reaction mixture. Representative acids include, but are not limited to, formic acid, acetic acid, citric acid, lactic acid, oxalic acid, trifluoroacetic acid, hydrofluoric acid, hydrochloric acid, hydrobromice acid, hypochlorous acid, perchloric acid, sulfuric acid, nitric acid, phosphoric acid, chromic acid, boric acid, methanesulfonic acid, benzenesulfonic acid, p-toluenesulfonic acid, triflouromethanesulfonic acid, or camphorsulfonic acid. In some embodiments, the acid can be hydrofluoric acid, hydrochloric acid, hydrobromic acid, hypochloric acid, sulfuric acid, nitric acid, phosphoric acid, hexafluorophosphoric acid, methanesulfonic acid, benzenesulfonic acid, p-toluenesulfonic acid, trifluoromethanesulfonic acid, fluoroacetic acid, or trifluoroacetic acid. In some embodiments, the acid can be hydrochloric acid.

Any suitable amount of acid can be used to reduce the pH of the reaction mixture containing the 3-(hydroperoxy)propanoic acid. For example, the pH of the reaction mixture containing the 3-(hydroperoxy)propanoic acid can be reduced to a pH less than 7.0, 6.0, 5.0, 4.0, or less than about 3.0. In some embodiments, the pH of the reaction mixture containing the 3-(hydroperoxy)propanoic acid is less than 7.0.

In some embodiments, the 3-(hydroperoxy)propanoic acid can be extracted by any suitable method. For example, the 3-(hydroperoxy)propanoic acid can be extracted via continuous extraction using ether as the extraction solvent.

In some embodiments, the method of preparing 3-hydroxypropanoic acid includes forming the reaction mixture comprising levulinic acid, hydrogen peroxide, and potassium hydroxide, wherein the reaction mixture is at about room temperature, thereby preparing 3-(hydroperoxy)propanoic acid, contacting the reaction mixture with hydrochloric acid such that the pH of the reaction mixture is less than 7.0, isolating the 3-(hydroperoxy)propanoic acid via extraction, and forming the second reaction comprising the 3-(hydroperoxy)propanoic acid, hydrogen and palladium on carbon, under conditions suitable to form the 3-hydroxypropanoic acid.

Any suitable reaction time can be used in the method of the invention. In general, reactions are allowed to run for a time sufficient for consumption of the starting material and conversion to the desired product, or until conversion of the starting material comes to a stop. Reactions are typically allowed to run for any amount of time ranging from a few minutes to several hours. Reactions can be run, for example, for anywhere between 5 minutes and 48 hours. Reactions can be run for about 5 minutes, or about 10, 15, 20, 30, 45, 60, or more minutes. Reactions can be run for about 1, 2, 3, 4, 5, or more hours.

IV. Examples

Materials and Methods.

Levulinic acid (98%), sulfuric acid (98%), sodium thiosulfate, potassium iodide, palladium on activated carbon (10 wt %), methyl iodide, and silver oxide were all purchased from Sigma Aldrich and used as received. Trifluoroacetic acid (99%), diethyl ether, and dichloromethane were purchased from Fischer Scientific. Hydrogen peroxide (30% aq) was purchased from Macron Chemicals. Hydrochloric acid (37% aq) was purchased from EMD Chemicals. Potassium hydroxide (technical, 87%) was purchased from Fisher Scientific.

Example 1. Oxidation of Levulinic Acid to Succinic Acid with Hydrogen Peroxide in 3M Sulfuric Acid

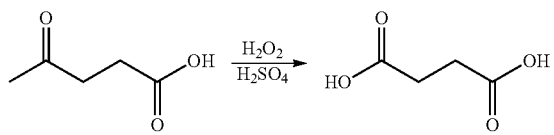

Levulinic acid (2.00 g, 17.2 mmol) was dissolved in 3M $H_2SO_4$ (20 mL) and 30% aq $H_2O_2$ (8 mL) was carefully added. The colorless solution was placed in an oil bath at 90° C. and stirred for 3.5 h. Additional 30% aq $H_2O_2$ (2.0 mL) was added, followed 20 min later by another aliquot of 30% aq $H_2O_2$ (2.0 mL). After 20 min the mixture was cooled to RT and a measured quantity of 1,4-dioxane was added as an internal standard. The $^1$H NMR spectrum was measured and the yields were determined as follows: succinic acid (48%), acetic acid (50%), formic acid (24%) and methanol (17%).

Example 2. Oxidation of LA by Hydrogen Peroxide in TFA

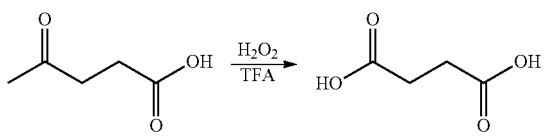

Levulinic acid (2.00 g, 17.2 mmol) was dissolved in TFA (40 mL) and 30% aq $H_2O_2$ (2.0 mL) was carefully added. The flask was mounted with a water-cooled condenser and −78° C. volatiles trap, and the colorless mixture was placed in an oil bath at 90° C. and stirred for 20 min. Additional 30% aq $H_2O_2$ (8.0 mL) was added portionwise at a rate of 2 mL every 20 min. The reaction was allowed to stir a further 20 min after the final addition, at which point the LA had been completely consumed as indicated by $^1$H NMR analysis. The mixture was cooled to room temperature and a measured amount of 1,4-dioxane was added as an internal standard. The $^1$H NMR spectrum was measured and the yields were determined as follows: succinic acid (62%), acetic acid (43%), 3-hydroxypropanoic acid (9%), and formic acid (45%). Methyl trifluoroacetate (45%) was obtained in the cold trap. The volatiles were evaporated to give a white solid which was triturated with $Et_2O$ (2×2 mL) to give succinic acid (1.22 g, 60%). $^1$H NMR δ: 2.64 (4H). $^{13}$C NMR δ: 176.9, 28.58.

Example 3. Scale-Up of the Oxidation of LA by Hydrogen Peroxide in TFA

Levulinic acid (10.00 g, 86.12 mmol) was dissolved in TFA (200 mL) and 30% aq $H_2O_2$ (10 mL) was carefully added. The flask was mounted with a water-cooled condenser and −78° C. volatiles trap, and the colorless mixture was placed in an oil bath at 90° C. and stirred for 20 min. Additional 30% aq $H_2O_2$ (40 mL) was added portionwise at a rate of 10 mL every 20 min. The reaction was allowed to stir a further 30 min after the final addition, at which point the LA had been completely consumed as indicated by $^1$H NMR analysis. The mixture was cooled to room temperature and a measured amount of 1,4-dioxane was added as an internal standard. The volatiles were evaporated under reduced pressure to give a white solid. The crude product was triturated with 1:1 $Et_2O$/DCM (3×6 mL) to give succinic acid (6.00 g, 59%). In the cold trap, methyl trifluoroacetate was isolated as a colorless oil (4.40 g, 40%).

Example 4. Direct Oxidation of Levulinic Acid to 3-Hydroxypropanoic Acid (HPA) with Hydrogen Peroxide

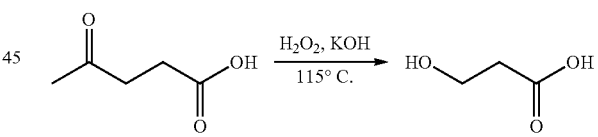

Levulinic acid (2.0 g, 17.3 mmol) was dissolved in 30% aq $H_2O_2$ (6 mL) at 0° C. and KOH (1.0 g) was added portionwise. The flask was then equipped with a condenser and a volatiles trap and placed in an oil bath preheated to 115° C. After 10 min, additional KOH (1.0 g) was added portionwise followed by 30% aq $H_2O_2$ (1 mL). Once gas evolution had ceased (1-2 min), additional KOH (1.0 g) was added portionwise followed slowly by 30% aq $H_2O_2$ (7 mL). Once gas evolution had again ceased (1-2 min), additional KOH (1.0 g) was added portionwise followed slowly by 30% aq, $H_2O_2$ (6 mL). The reaction mixture was then allowed to stir at 115° C. for 50 min. Finally, additional KOH (0.5 g) was added portionwise followed slowly by 30% aq $H_2O_2$ (4 mL). The solution was stirred for an additional 10 min then allowed to cool to room temperature. A measured amount of 1,4-dioxane was added as internal standard and the reaction mixture was analyzed by $^1$H NMR. The product yields determined by this method were HPA (47%), acetic acid (89%), formic acid (29%), and methanol (9%). Acetone (ca. 1%) was collected from the volatiles trap. The mixture was cooled in an ice bath and acidified to pH 3-4 using conc HCl. The volatiles were evaporated under reduced pressure to give a white solid. The HPA product was extracted from this mixture using ether (3×50 mL). After the evaporation of the solvent, HPA was obtained as a colorless oil (700 mg, 45%). $^1$H NMR (600 MHz, D$_2$O) δ 3.83 (t, J=6.0 Hz, 2H), 2.59 (t, J=6.0 Hz, 2H); $^{13}$C NMR (150 MHz, D$_2$O) δ 175.9, 71.9, 32.8.

Example 5. Preparation of 3-hydroxypropanoic Acid from Levulinic Acid

This example describes the preparation of 3-hydroxypropanoic acid from levulinic acid, via 3-(hydroperoxy)propanoic acid.

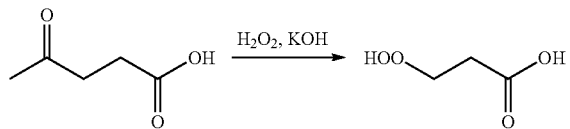

Oxidation of Levulinic Acid to 3-(hydroperoxy)propanoic Acid with Hydrogen Peroxide Levulinic acid (4.00 g, 34.5 mmol) was dissolved in 30% aq H$_2$O$_2$ (24 mL) at 0° C. To the resulting solution was added dropwise with stirring 5.2 M aq KOH (28.8 mL, 150 mmol). The ice bath was replaced by a water bath and the mixture was allowed to stir for 1.5 h. The water bath was then removed and the mixture was allowed to stir an additional 2.5 h. Finally, another portion of 30% aq H$_2$O$_2$ (8.0 mL) was added. The solution was allowed to stir until NMR indicated full conversion of the levulinic acid, ca. 2 h after the final addition of H$_2$O$_2$. The mixture was cooled in an ice bath and acidified to pH 3-4 with conc HCl. A measured amount of 1,4-dioxane was added as internal standard and the reaction mixture was analyzed by $^1$H NMR. The product yields determined by this method were 3-(hydroperoxy)propanoic acid (82%), acetic acid (80%), 3-hydroxypropanoic acid (5%) and formic acid (4%). The 3-(hydroperoxy)propanoic acid product could be isolated by continuous extraction (5 h) of the acidified reaction mixture using ether as the extraction solvent. After the evaporation of the volatiles, 3-(hydroperoxy)propanoic acid was obtained as a colorless oil (2.91 g, 80%) along with a small quantity of 3-hydroxypropanoic acid. $^1$H NMR (300 MHz, D$_2$O) δ 4.18 (t, J=5.9 Hz, 2H), 2.67 (t, J=5.9 Hz, 2H); $^{13}$C NMR (75 MHz, D$_2$O) δ 175.9, 71.9, 32.8.

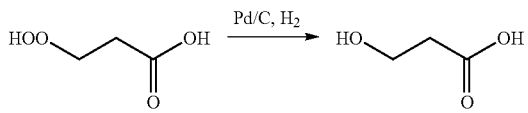

Hydrogenation of 3-(hydroperoxy)propanoic Acid to 3-hydroxypropanoic Acid

The above-produced 3-(hydroperoxy) propanoic acid (2.90 g, 27.4 mmol) was dissolved in 30 mL of methanol. Palladium on activated carbon (10 wt % Pd, 30 mg) was added and the mixture was carefully evacuated and then backfilled with hydrogen three times. The reaction flask was pressurized to 3.8 atm hydrogen and shaken for 40 min. The mixture was filtered through a short plug of Celite, which was further rinsed with methanol (30 mL). The solvent was evaporated to give 3-hydroxypropanoic acid (HPA) as a colorless oil (2.48 g, 100%). $^1$H NMR (600 MHz, D$_2$O) δ 3.83 (t, J=6.0 Hz, 2H), 2.59 (t, J=6.0 Hz, 2H); $^{13}$C NMR (150 MHz, D$_2$O) δ 175.9, 71.9, 32.8.

Example 6. Derivatization of 3-(hydroperoxy)propanoic Acid

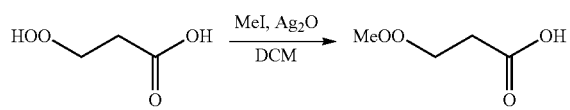

A mixture of 3-(hydroperoxy)propanoic acid (410 mg, 3.9 mmol), silver oxide (2.5 g, 11 mmol), methyl iodide (1.5 g, 11 mmol) and DCM (15 mL) was stirred in the dark for 16 h at room temperature. The reaction was filtered through a short plug of Celite and the solvent was evaporated under reduced pressure. The residue was purified by column chromatography on silica gel to give methyl 3-(methylperoxy)propanoate as a colorless oil (150 mg, 29%). $^1$H NMR (600 MHz, CDCl$_3$) δ 4.23 (t, J=6.2 Hz, 2H), 3.79 (s, 3H), 3.68 (s, 3H), 2.64 (t, J=6.2 Hz, 2H); $^{13}$C NMR (150 MHz, CDCl$_3$) δ 171.6, 69.4, 62.3, 51.8, 33.3.

Example 7. Iodometric Titration of 3-(hydroperoxy)propanoic Acid

A sample of 3-(hydroperoxy)propanoic acid in EtOAc was filtered through a plug of silica gel. The solvent was evaporated and the residue was dissolved in D$_2$O. A measured amount of 1,4-dioxane was added as internal standard. The quantity of 3-(hydroperoxy)propanoic acid was determined to be 1.61 mmol by $^1$H NMR analysis. To this solution was added potassium iodide (1.07 g, 6.44 mmol) and 1.0 M aq HCl (20 mL). The mixture was stirred in the dark for 20 min. It was found that 32.4 mL of 0.100 M sodium thiosulfate solution (3.24 mmol) was required to titrate the generated iodine to a colorless endpoint with a starch indicator.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A method of preparing a carboxylic acid, comprising:
    forming a reaction mixture comprising levulinic acid, an oxidant selected from peroxides, and an acid, wherein the acid is trifluoroacetic acid, under conditions suitable to prepare the carboxylic acid, wherein the carboxylic is succinic acid, wherein the reaction mixture is free of an oxidizing metal catalyst, and heating the reaction mixture at a temperature of from about 30° C. to about 100° C., thereby preparing the succinic acid.

2. The method of claim 1, wherein the oxidant is hydrogen peroxide.

3. The method of claim 1, wherein the acid is trifluoroacetic acid, and the oxidant is hydrogen peroxide; and the reaction mixture is heated at a temperature of from about 50° C. to about 100° C., thereby preparing succinic acid.

* * * * *